United States Patent [19]
Erickson et al.

[11] Patent Number: 5,746,217
[45] Date of Patent: May 5, 1998

[54] INTERSTITIAL FLUID COLLECTION AND CONSTITUENT MEASUREMENT

[75] Inventors: Brian J. Erickson, Woodbury; Michael E. Hilgers, Roseville; Tracy A. Hendrickson, Minnetonka; J. Edward Shapland, Shoreview; Frank A. Solomon, Plymouth; Mark B. Knudson, Shoreview, all of Minn.

[73] Assignee: Integ Incorporated, Roseville, Minn.

[21] Appl. No.: 555,314

[22] Filed: Nov. 8, 1995

Related U.S. Application Data

[60] Division of Ser. No. 321,305, Oct. 11, 1994, Pat. No. 5,582,184, which is a continuation-in-part of Ser. No. 136,304, Oct. 13, 1993, abandoned.

[51] Int. Cl.$^6$ ............................................. A61B 5/00
[52] U.S. Cl. ............................. 128/760; 128/771; 606/181
[58] Field of Search ................................ 128/760, 763, 128/770, 771; 604/51, 117, 289, 290; 606/181, 182

[56] References Cited

U.S. PATENT DOCUMENTS

| | | |
|---|---|---|
| 3,123,066 | 3/1964 | Brumley . |
| 3,136,310 | 6/1964 | Meltzer . |
| 3,208,452 | 9/1965 | Stern . |
| 3,338,239 | 8/1967 | Mausteller . |

(List continued on next page.)

FOREIGN PATENT DOCUMENTS

| | | |
|---|---|---|
| 160768 | 11/1985 | European Pat. Off. . |
| 0453283A1 | 10/1991 | European Pat. Off. . |
| 3708031 | 12/1987 | Germany . |
| 2033575 | 5/1980 | United Kingdom . |
| PCT/GB85/00095 | 9/1985 | WIPO . |
| PCT/DK91/00152 | 12/1991 | WIPO . |

OTHER PUBLICATIONS

Pp. 326–327 entitled "Method for Sampling Interstitial Fluid" by Ronald J. Korthuis and Aubrey E. Taylor from book entitled *Microcirculatory Technology*, edited by C.H. Baker et al., Orlando, Florida, Academic Press, Chapter 21, 1986.

Ash SR; Rainier JB; Zopp WE; Truitt RB; Janle EM; Kissinger Pt; Poulos JT. A Subcutaneous capillary filtrate collector for measurement of blood chemistries. Jul.–Sep. 1993, 39 (3) pM699–705.

Brace RA; Guyton AC; Taylor AE. Reevaluation of the Needle Method for Measuring Interstitial Fluid Pressure. Am J. Physio (United States) Sep. 1975, 229 (3) p603–7.

Gilanyi M; Ikrenyi C; Fekete J; Ikrenyi K; Kovach AG. Ion Concentrations in Subcutaneous Interstitial Fluid: Am J. Physio (United States) Sep. 1988, 255 (3 Pt 2) pF513–9.

Kayashima S; Arai T; Kikuchi M; Nagata N; Kuriyama T; Kimura J. Suction Effusion Fluid From Skin and Constituent Analysis. Am J Physiol (United States) Nov. 1992, 263 (5 Pt 2) pH1623–7.

Petersen LJ; Kristensen JK; Beulo J. Microdialysis of the Interstitial Water Space in Human Skin. J Invest Dermatol (United States) Sep. 1992, 99 (3) p357–60.

Turner APF, and Pickup JC. Diabetes Mellitus: Biosensors for Research and Managment. Biosensors 1 (1985): 85–115.

Wiig H. Evaluation of Methodologies for Measurement of Interstitial Fluid Pressure. Crit Rev Biomed Eng (United States) 1990, 18 (1) pp. 27–54.

(List continued on next page.)

*Primary Examiner*—Max Hindenburg
*Attorney, Agent, or Firm*—Merchant, Gould, Smith, Edell, Welter & Schmidt, P.A.

[57] ABSTRACT

An apparatus and method is disclosed for obtaining and measuring constituents in a sample of body fluid. The apparatus includes a member which is sized to penetrate into at least the dermal layer of skin to collect a sample of body fluid located within the dermal layer.

11 Claims, 15 Drawing Sheets

U.S. PATENT DOCUMENTS

| | | |
|---|---|---|
| 3,958,560 | 5/1976 | March . |
| 4,014,321 | 3/1977 | March . |
| 4,195,641 | 4/1980 | Johnes et al. . |
| 4,200,110 | 4/1980 | Peterson . |
| 4,407,290 | 10/1983 | Wilbur . |
| 4,517,978 | 5/1985 | Levin . |
| 4,622,974 | 11/1986 | Coleman et al. . |
| 4,637,403 | 1/1987 | Garcia et al. . |
| 4,648,408 | 3/1987 | Hutcheson et al. . |
| 4,655,225 | 4/1987 | Dahne et al. . |
| 4,660,971 | 4/1987 | Sage et al. . |
| 4,685,463 | 8/1987 | Williams . |
| 4,703,756 | 11/1987 | Gough et al. . |
| 4,704,029 | 11/1987 | Van Heuvelen . |
| 4,730,622 | 3/1988 | Cohen . |
| 4,750,830 | 6/1988 | Lee . |
| 4,805,623 | 2/1989 | Jobsis . |
| 4,873,993 | 10/1989 | Meserol et al. . |
| 4,882,492 | 11/1989 | Schlager . |
| 4,883,068 | 11/1989 | Dechow . |
| 4,901,728 | 2/1990 | Hutchison . |
| 4,953,552 | 9/1990 | DeMarzo . |
| 4,954,318 | 9/1990 | Yafuso et al. . |
| 4,960,467 | 10/1990 | Peck . |
| 4,981,779 | 1/1991 | Wagner . |
| 5,002,054 | 3/1991 | Ash et al. . |
| 5,014,718 | 5/1991 | Mitchen . |
| 5,029,583 | 7/1991 | Meserol et al. . |
| 5,054,499 | 10/1991 | Swierczek . |
| 5,066,859 | 11/1991 | Karkar et al. . |
| 5,070,886 | 12/1991 | Mitchen et al. . |
| 5,079,421 | 1/1992 | Knudson et al. . |
| 5,115,133 | 5/1992 | Knudson . |
| 5,146,091 | 9/1992 | Knudson . |
| 5,179,951 | 1/1993 | Knudson . |
| 5,201,324 | 4/1993 | Swierczek . |
| 5,231,993 | 8/1993 | Haber et al. . |
| 5,320,607 | 6/1994 | Ishibashi . |
| 5,470,757 | 11/1995 | Gagnon et al. . |

OTHER PUBLICATIONS

Wolfson Jr Sk, Tokarsky JF, Yao SJ, and Krupper MA. Glucose Concentration at Possible Sensor Tissue Implant Sites. Diabetes Care 5, No. 3 (1982): 162.

Article entitled "Blood Glucose Measurement by Multiple Attenuated Total Reflection and infrared Absorption Spectroscopy". I.E.E.E. Transaction on Biomedical Engineering, vol. 37 No. 5, May, 1990.

Article entitled Determination of Physiological Levels of Glucose in an Equeous Matrix with Digitally Filtered Four–Year Transfer Near–Infrared Spectra, by Arnold and Small. Anal Chem. 1990.

Article entitled "New Non–Invasive Transcutaneous Approach to Blood Glucose Monitoring". I.E.E.E. Transactions on Biomedical Engineering, vol. 38, No. 8, Aug. 1991.

Article entitled "Use of Capillary Filtrate Collector for Monitoring Glucose in Diabetics". Artif. Intern. Organs 1987.

Article entitled "Suction Blister Device for Separation of Viable Epidermis from Dermis", vol. 50, No. 2, Journal of Investigative Dermatology, 1968.

Article entitled "Subcutaneous Capillary Filtrate Collector of Measurement of Blood Glucose", ASAIO Journal, 1992, pp. M416–M420.

Article entitled "Toward Continuous Glucose Monitoring: In Vivo Evaluation of Miniaturized Glucose Sensor Implanted For Several Days From Rate Subcutaneous Tissue" (Diabetologia Glen 1992 35:224–230.

Article entitled "An Overview of Minimally Invasive Technologies", by Barry H. Ginsberg, Clincial Chemistry, vol. 38, No. 9, 1992, pp. 1596–1600.

P. 26 of Diabetes Forecast, May, 1993, under Sections "Glucose Sensors" and Like An Injection.

Article entitled "Quantitative Analysis of Aqueous Solutions by FTIR Spectroscopy of Dry Extract". N. DuPuy et al., SPIE, vol. 1575, 8th International Conference on Fourier Transform Spectroscopy (1991), pp. 501–502.

P. 60 of brochure of Gelman Science (1993) showing Nylaflow, Catalog P/N 32378.

FIG. 1
FIG. 2
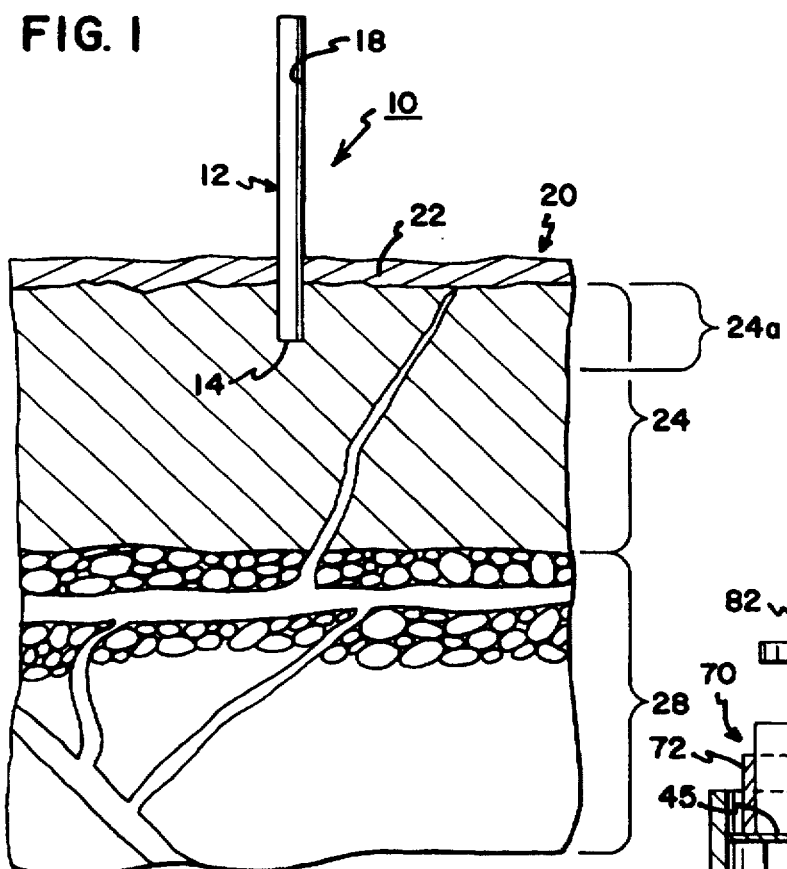
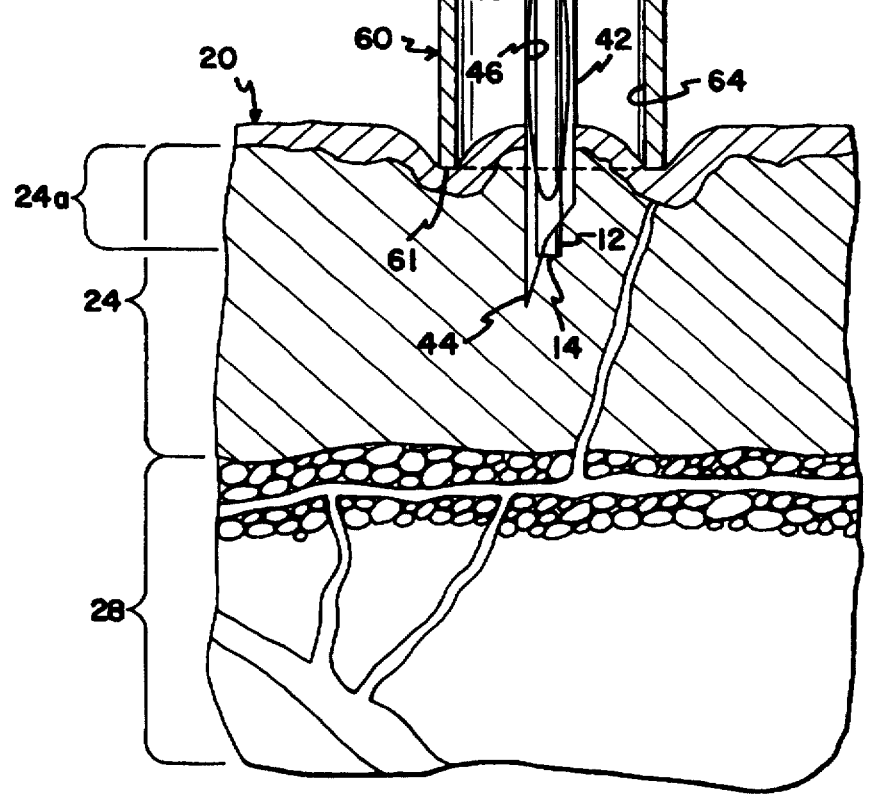

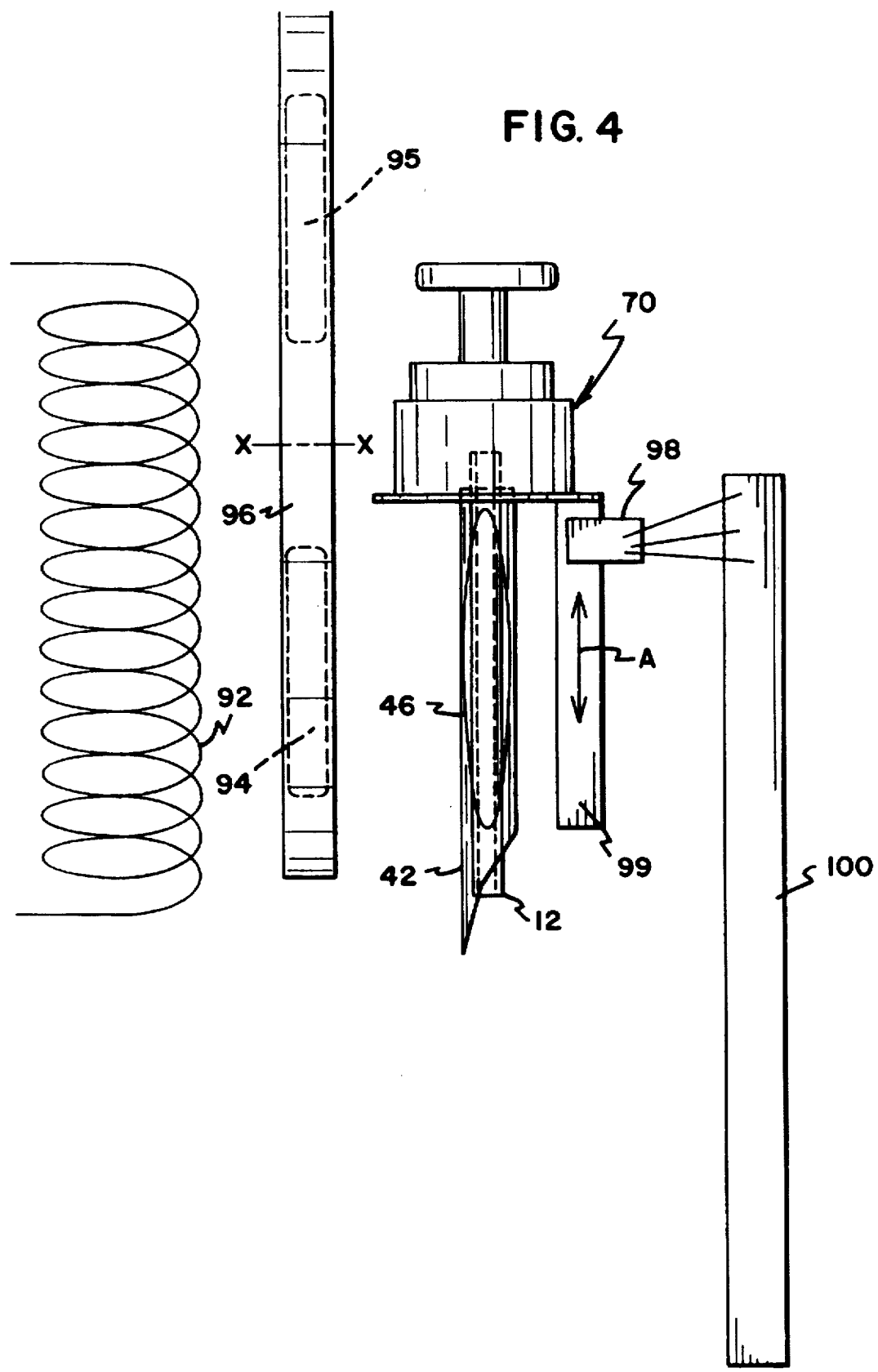

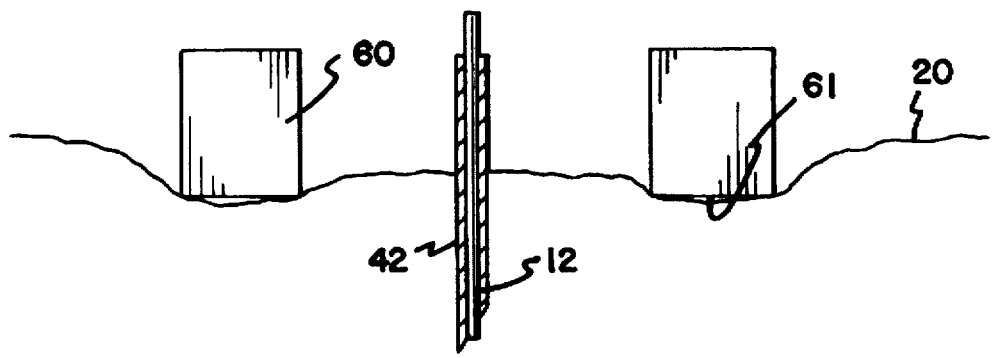
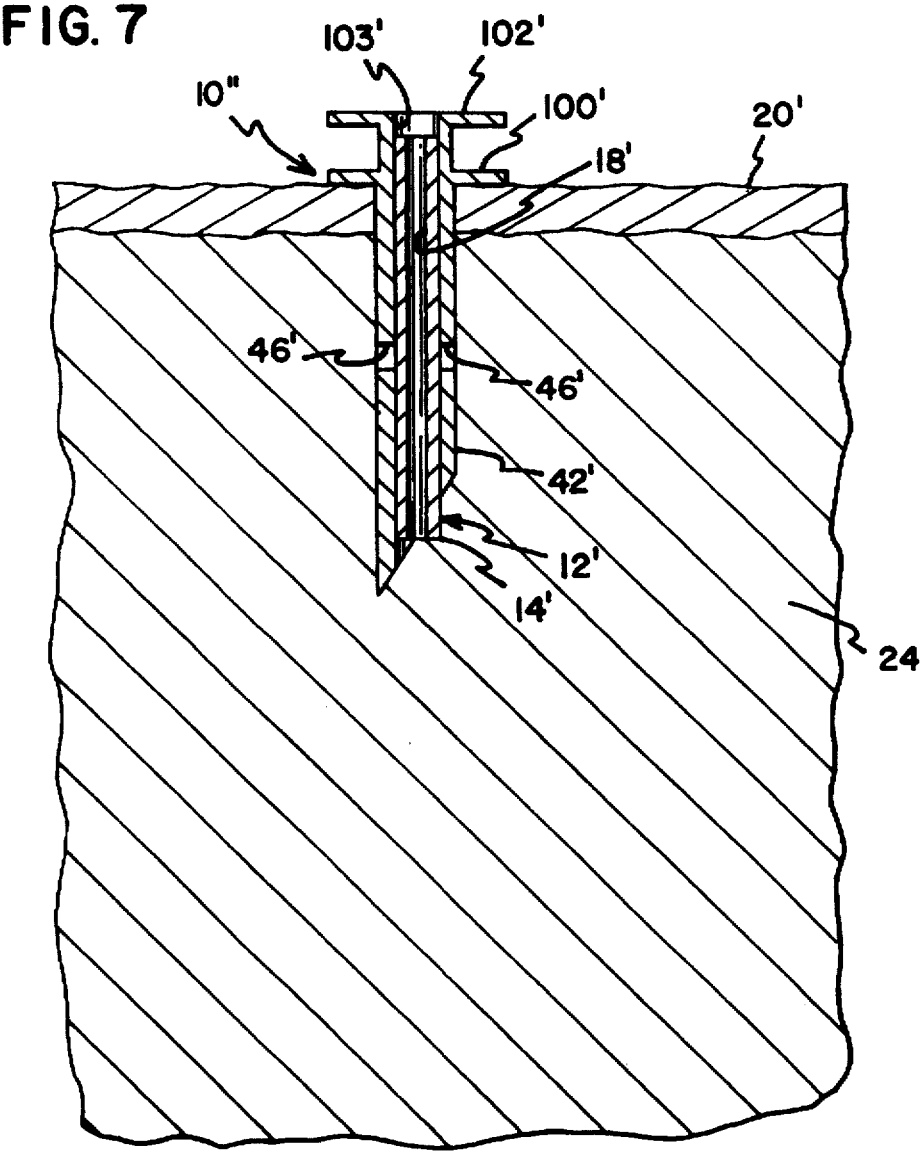

INTERSTITIAL FLUID COLLECTION AND CONSTITUENT MEASUREMENT

I. CROSS-REFERENCE RELATED APPLICATIONS

This is a division of application Ser. No. 08/321,305, filed Oct. 11, 1994, now U.S. Pat. No. 5,582,184 which is a continuation-in-part of Ser. No. 08/136,304, filed Oct. 13, 1993, now abandoned.

II. BACKGROUND OF THE INVENTION

1. Field of the Invention

The present invention relates to an apparatus for testing body fluid constituents. More particularly, the present invention pertains to an apparatus for collecting body fluid for testing.

2. Description of the Art

The prior art has long been seeking procedures for testing and determining the level of blood constituents. Particularly, a great deal of attention has been spent on the development of techniques for measuring blood glucose.

Historically, blood glucose and other bodily analyte measurements were, and remain, invasive. Such measurements are generally made by withdrawing a blood sample and measuring the desired analyte within the blood or plasma. Blood samples can be withdrawn by inserting a needle into a major artery or, more commonly, a vein. A syringe or other device is used to provide any necessary suction and collect the blood sample. Needles used for this sampling technique must be long enough to pass through the skin, subcutaneous tissue, and blood vessel wall. The needle must also have a sufficient diameter to allow timely collection of the blood sample without causing hemolysis of the blood. Minimal diameter to meet these criteria is generally 20 gauge or larger diameter. Such direct vascular blood sampling has several limitations, including pain, hematoma and other bleeding complications, and infection. In addition, due to the vascular damage resulting from the needle puncture, sampling could not be repeated on a routine basis. Finally, it is extremely difficult for patients to perform a direct vascular puncture on themselves.

The other common technique for collecting a blood sample is to cut or lance the skin and the subcutaneous tissue, including the small, underlying blood vessels, to produce a localized bleeding on the body surface. A lancet, knife, or other cutting device is required. The blood on the body surface can then be collected into a small tube or other container. The fingertip is the most frequently used site to collect blood in this method due to the large number of small blood vessels located in the region. One method is shown in U.S. Pat. No. 4,637,403. This sampling method also suffers from several major disadvantages, including pain and the potential for infection and other problems associated with repeated sampling for a confined area. Pain is a major disadvantage since the fingertip has a large concentration of nerve endings. Also, there is a limited body surface area from which to take these samples and measurement on a high frequency basis.

Because the prior art invasive techniques are painful, patients frequently avoid having blood glucose measured. For diabetics, the failure to measure blood glucose on a prescribed basis can be very dangerous. Also, the invasive techniques, which would result in lancing blood vessels, create an enhanced risk for disease transmission.

Attempts have been made to develop glucose and other analyte sensors for implantation in the human body. Implanted glucose sensors would be primarily to control insulin infusion pumps or provide continuous, chronic monitoring. Development of a permanently implanted or long-term, chronic implanted sensor has been unsuccessful. Attempts to develop short-term implantable sensors (up to 2-3 days) have also met with very limited success. Most implantable sensors are based on measuring various products from chemical reactions between agent(s) located on or within the sensor and the desired analyte. Implanted glucose sensors have typically used the glucose oxidase reaction to measure the amount of glucose, as described in U.S. Pat. No. 5,108,819. Such implantable glucose sensors have been intended for insertion through the epidermis and dermis to the subcutaneous tissue. An alternative location previously described for chronic sensor implant is the peritoneal cavity. All such implanted sensors require direct or telemetered connection to a measurement instrument, usually located external the body.

All implanted sensors are faced with several major problems. First, all foreign materials, including materials incorporated into a glucose sensor, produce unwanted body reactions. Such reactions include the formation of fibrotic tissue around the sensor which alters the sensor's contact with normal body fluids and analytes, such as glucose. The body's natural defense mechanism may also have a direct "poisoning" effect upon the sensor's operation by interfering with the chemical reactions required by chemical-based sensors. As with any implanted object, implanted sensors may also initiate other bodily reactions including inflammation, pain, tissue necrosis, infection, and other unwanted reactions.

Implanted sensors require certain chemicals and chemical reactions to determine the level of analyte in the surrounding medium. These chemical reactions are the source of the other major problem facing any implantable sensor. Chemically-based sensors require products to be consumed and other products to be produced as part of the sensor's normal operations. Therefore, the sensors can quickly be depleted of the chemical agents required to sustain the desired chemical reactions. Secondly, by-products are given off as a result of the basic chemical reaction. These by-products often "poison" the sensor or cause other unwanted tissue reactivity. Because of these severe limitations, implanted sensors are not practical. Finally, such implanted sensors are painful to implant and are a source of infection.

By withdrawing the body fluid containing the glucose or other analyte and making the measurement outside the body, these aforementioned sensor based problems can be avoided. Specifically, there is no concern about the chronic tissue response to the foreign sensor material or the limited operational life of the sensor due to the consumption of reaction agents or the production of unwanted by-products from that reaction.

In view of the risk associated with invasive techniques, the prior art has sought to develop non-invasive blood glucose measurement techniques. An example of such is shown in U.S. Pat. No. 4,882,492 to Schlager. Schlager teaches a non-invasive near-infrared measurement of blood. Schlager is particularly directed to the measurement of blood glucose levels. The Schlager patent recognizes that certain wavelengths of light in the near-infrared spectrum are absorbed by glucose. Modulated light is directed against a tissue (shown as an earlobe). The light is either passed through the tissue or impinged on a skin surface. The light is spectrally modified in response to the amount of analyte (for example, glucose) in the blood and tissue. The spectrally modified light is split with one beam passed through a correlation cell. The other beam is passed through a reference cell. The intensity of the beams passing through the correlation cell and the reference cell are compared to calculate a glucose concentration in the sample. Other non-invasive blood glucose methods are shown in U.S. Pat. Nos. 4,805,623, 4,655,225, 4,014,321 and 3,958,560.

One drawback of prior art non-invasive systems is that by passing the infrared light through a complex medium (such as an earlobe) very complex data is generated. Algorithms must be developed to manipulate the data in order to attempt to provide reliable indications of blood glucose measurements. Also, such devices may require exact placement of the measuring device (e.g., precise placement on a patient's finger or near an earlobe) to minimize measurement error. Such devices may also be difficult to calibrate. To date, the prior art has not developed commercially available non-invasive methods which provide accurate data.

In addition to the foregoing, applicants' assignee is the owner of various patents pertaining to blood glucose measurement. For example, U.S. Pat. No. 5,179,951 to Knudson dated Jan. 19, 1993 teaches an invasive blood glucose measurement where infrared light is passed through a sample of blood by use of an implanted catheter. Similarly, U.S. Pat. No. 5,079,421 teaches such a system.

U.S. Pat. No. 5,146,091 teaches a non-invasive blood glucose measurement utilizing FTIR (Fourier Transform Infrared) techniques to determine blood glucose levels and U.S. Pat. No. 5,115,133 which directs infrared light to the eardrum. As indicated in the aforementioned commonly assigned patents, the testing wavelength includes a glucose sensitive wavelength of about 500 to about 4,000 wave numbers ($cm^{-1}$). Preferably, the glucose absorbable wavelength is about 1,040 wave numbers.

It is an object of the present invention to provide an enhanced technique for collecting a sample fluid and for measuring fluid constituents in the sample.

III. SUMMARY OF THE INVENTION

According to a preferred embodiment of the present invention, an apparatus and method are disclosed for collecting and measuring constituents in a sample of body fluid. The method includes urging a sampler against a subject's skin. The sampler includes a penetration member which is sized to penetrate the subject's skin upon the urging of the sampler. A sample of fluid is drawn along the penetration member. The sample is tested for desired constituents such as glucose concentration.

In one embodiment, a body fluid is drawn from the dermal layer of skin. The apparatus includes a conduit which is sized to penetrate into the dermal layer. Light having a wavelength absorbable by the constituent is passed through the conduit. The amount of absorption indicates the amount of constituent in the drawn sample. Alternative embodiments of the present invention include drawing a sample of fluid and depositing the sample on, within or between a membrane(s) or substrate(s). The sample deposited on, within or between the membrane(s) or substrate(s) is tested for constituents.

The present invention provides numerous advantages over the prior art techniques. Compared to the prior art invasive and non-invasive techniques, the present invention may more accurately be referred to as a minimally invasive technique.

The present invention utilizes a small needle for drawing a minute amount of fluid. Preferably, the fluid is drawn from the dermal layer of the skin. The dermal layer of the skin has smaller nerves compared to the subcutaneous layer of the skin. Accordingly, the pain associated with prior art invasive techniques is substantially avoided resulting in increased probability of a patient's compliance with prescribed testing. Also, the total body area from which a sample may be taken is not restricted to a fingertip. Furthermore, smaller blood vessels outside of the subcutaneous layer result in minimal or no blood loss and blood vessel rupture by reason of the testing. These and other advantages of the present invention will become apparent through the following detailed description of the invention.

IV. BRIEF DESCRIPTION OF THE DRAWINGS

FIG. 1 is a front sectional view of an apparatus according to the present invention shown inserted into a layer of skin;

FIG. 2 is a detailed sectional view of a portion of a preferred embodiment of the present invention shown inserted in a layer of skin;

FIG. 4 is a side elevation view of a portion of the apparatus of FIG. 3 shown in an analysis apparatus (shown schematically);

FIG. 6 is an enlarged side sectional view of the apparatus of FIG. 2;

FIG. 7 is a detailed sectional view of an alternative embodiment of the present invention shown inserted in a layer of skin;

V. DESCRIPTION OF PREFERRED EMBODIMENTS

A. Fluid Sampling Generally

Figure 3:
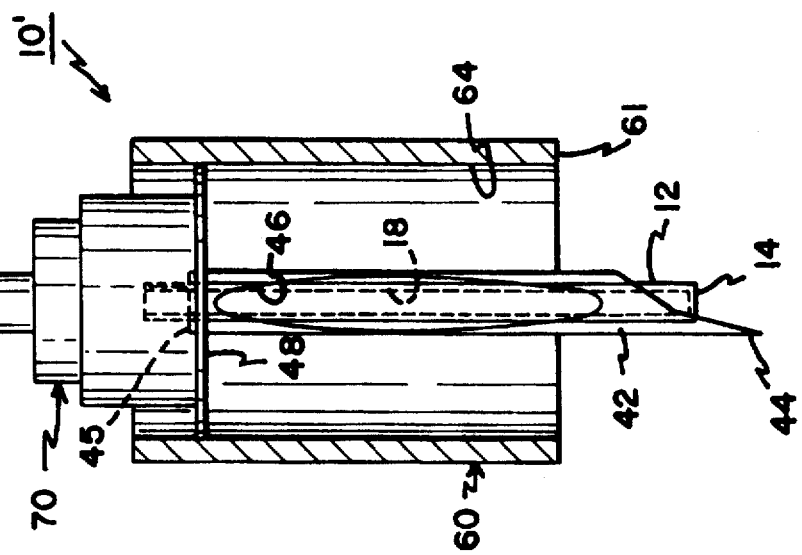
FIG. 3 is a detailed sectional view of the apparatus shown in FIG. 2.

Referring now to FIG. 1, an apparatus 10 is shown for use in minimally-invasive testing for a body fluid constituent. While the illustrated application is a preferred embodiment, it will be appreciated that the salient features are applicable to a wide variety of body constituents found in body fluid.

In FIG. 1, the apparatus 10 according to the present invention is shown in its most elementary structure for ease of illustration. The apparatus 10 is for collecting a sample of fluid.

The apparatus 10 includes a penetration member in the form of a conduit 12, preferably a hollow capillary type tube, which is open at both ends and which is inserted into a layer of skin 20. As shown in FIG. 1, the structure of the skin 20 includes three distinct layers, the epidermis 22, which is the top thin layer, the dermis 24, or middle layer, and the subcutaneous layer 28. Commonly, the epidermis is about 100 microns thick, the dermis 24 is about 2,000–3,000 microns thick.

The collection apparatus 10 is designed and dimensioned for insertion into the dermal layer 24 of the skin without penetration into the subcutaneous layer 28. The dermal layer 24 generally consists of a dense bed of connective tissue including collagen fibers. It is currently believed bodily fluid is present in the interstitial space defined between the collagen fibers and cells. This interstitial, dispersed bodily fluid includes constituents, such as glucose, in a concentration representative of the constituent's concentration in other bodily fluids, such as blood. Thus, this interstitial fluid may be tested to accurately measure the level of constituents present in an individual's bodily fluids (e.g., blood sugar levels). While it is believed low blood (i.e., few or no red cells) interstitial fluid is preferred any body fluid may be collected through the present invention. However, for ease of illustration, the body fluid will be referred to herein as interstitial fluid.

According to the present invention, the capillary tube 12 is inserted into the dermal layer 24 of the skin to collect a sample of interstitial fluid for subsequent testing of a level of a constituent in the interstitial fluid. In order to collect interstitial fluid with minimal pain, a capillary tube 12 with inside diameter of 114 microns and outside diameter of 140 microns is presently preferred. In the preferred embodiment, the interstitial fluid is to be tested to measure the level of glucose in the fluid.

The capillary tube 12 is inserted to a position in which the distal end 14 of the tube 12 is approximately in the upper third portion 24a of the dermal layer 24 to ensure the subcutaneous layer 28 is not penetrated. The capillary tube 12 is disposed in this position while interstitial fluid located adjacent to the distal end 14 of the tube 12 is drawn up inside the tube 12 and retained within the internal passageway 18 of the tube 12.

B. IR Testing Generally

Discussed more fully with respect to the embodiments of FIGS. 11–22, the collected sample of interstitial fluid may be deposited on a membrane for subsequent IR testing or may be tested through other means (including electro-chemical or colormetric). The following discussion discusses IR testing through the tube 12 as one means of constituent testing.

For IR testing of a sample in tube 12, the capillary tube 12 includes at least a section of the tube 12 which is selected to pass certain predetermined light wavelengths (e.g.— wavelengths which are absorbable by constituents which are to be measured). This allows for spectrophotometric analysis of the constituents in the interstitial fluid without the need for pipetting or transferring the fluid in any manner. For purposes of this application and any appended claims, the term "light" is intended to mean both the visible and invisible (e.g., infrared) spectra.

Once the interstitial fluid is retained in the capillary tube 12, a testing light which includes wavelengths absorbable by the constituent to be tested, is generated and directed through the capillary tube 12 containing the constituent of the interstitial fluid. By measuring the amount of absorption of the absorbable wave length, the level of the constituent in the interstitial fluid may be calculated.

In one embodiment, the entire tube 12 is made of a material to pass a test wavelength. When testing for glucose with infrared energy at 1040 wavenumbers, a preferred material is nylon, polyethylene or polyamide, which is at least partially transparent to infrared light wavelengths. However, while the specifically mentioned materials are currently preferred, it will be appreciated other materials may suffice. Infrared light having a wavelength absorbable by blood glucose then is directed through the capillary tube to measure the level of glucose in the interstitial fluid.

C. Detailed Discussion of Embodiment for Testing Sample In Tube

Referring to FIGS. 2 and 3, a preferred embodiment of an apparatus 10' for collecting interstitial fluid is shown. It is appreciated that while this embodiment illustrates a structure for inserting the capillary tube 12 to a predetermined depth within the dermal layer 24 of the skin 20 and drawing interstitial fluid into the capillary tube 12, numerous other devices could be effectively utilized in accordance with the principals of the present invention to accomplish the same results.

As shown in FIGS. 2 and 3, the collection apparatus 10' includes a capillary tube 12 and a hollow needle 42. The capillary tube 12 is securely retained within the needle 42 so that the distal end 14 of the capillary tube 12 is disposed adjacent the insertion tip 44 of the needle 42. Preferably the tip 44 of the needle 42 is designed to facilitate quick and efficient penetration of the skin. In the preferred embodiment, the needle 42 is selected with a small diameter (30 gauge) to minimize or eliminate the pain of insertion.

The needle 42 includes opposing axially extending slots 46 which expose a portion of the capillary tube 12 such that a testing light may be directed through slots 46 and through capillary tube 12 while the capillary tube 12 is retained within the needle 42. It is noted that while the preferred embodiment provides for testing of the constituent in the interstitial fluid with the capillary tube 12 retained in the needle 42, alternatively, the capillary tube 12 could be removed from the needle 42 after collection of the interstitial fluid for testing of the interstitial fluid constituents.

The collection apparatus 10' includes a spacer member 60 which is designed to control the depth of the penetration of the needle 42. The spacer member 60 has a generally cylindrical shape and encircles the needle 42. A proximal end 45 of the needle 42 is secured to a mounting plate 48 having an opening 52 (shown in FIG. 2 only) corresponding to the outer diameter of the needle 42 such that the needle is securely attached to the mounting plate 48. The mounting plate 48 is sized to fit within the spacer member 60. Preferably, the spacer member 60 includes mounting clips or other appropriate structure (e.g. an annular groove sized to receive a peripheral edge of plate 48) positioned on the inner wall 64 of the spacer member 60 to securely attach the mounting plate 48 to the spacer member 60. The tip 44 of the needle assembly and the distal end 14 of the capillary tube extend a predetermined distance beyond the bottom 61 of the spacer member 60.

In operation, the spacer member 60 is placed against the surface of the skin 20 such that the needle 42 penetrates into the skin. As shown in FIG. 2, with the spacer member 60 placed firmly against the skin surface, the tip 44 of the needle 42 extends into an upper portion 24a of the dermal layer 24 of skin. In the preferred embodiment, the tip 44 of the needle 42 is inserted such that the effective depth of the distal end 14 of the capillary tube 12 is about 0.7 mm. Generally, the dermal layer of the skin is 2-3 mm deep and thus the insertion of the capillary tube to a depth of 0.7 mm places the capillary in the upper third portion 24a of the dermal layer 24 and away from the subcutaneous layer 28. In this way, the capillary tube 12 is positioned to obtain a clean sample of interstitial fluid. If the capillary tube 12 were to be inserted further into the dermal layer 24, the potential for the capillary tube entering the subcutaneous level of the skin increases. The subcutaneous layer 28 of the skin includes fatty tissue cells, relatively large blood vessels and large nerves and, as currently believed by applicants, does not provide for a low blood sample of interstitial fluid. Thus, the present invention preferably positions the capillary tube 12 in the upper third portion 24a of the dermis 24 without extending through the dermis 24 into the subcutaneous layer 28 to minimize the pain of the insertion and while also obtaining a low blood sample of interstitial fluid.

In accordance with the present invention, once the capillary tube 12 is inserted into the dermal layer 24, interstitial fluid located adjacent to the distal end 14 of the capillary tube 12 is urged up into the capillary tube 12 and retained therein. This may be achieved through various methods. For example, capillary action, negative pressure, or compressing the skin 20 surrounding the apparatus 10 may all be utilized to urge interstitial fluid into the passageway 18 of the capillary tube 12.

A vacuum generating mechanism 70 may be provided to assist the flow of interstitial fluid into the capillary tube 12. Shown best in FIG. 2, the vacuum mechanism 70 includes an outer cylindrical wall 72 and a housing 74 defining an inner chamber 76. The outer wall 72 is secured to the mounting plate 48 of the needle 42 with the vacuum housing 74 movably disposed against the outer wall 72. The proximal end 17 of the capillary tube 12 and proximal end 45 of needle 42 extend into the inner chamber 76 of the housing 74. A seal 80 is provided between the needle 42 and the tube 12.

The vacuum mechanism 70 includes a plunger 82 which is secured to the housing 74 to move the housing between an upper and lower position. When the collection apparatus 10' is first placed against the skin so that a portion of the needle assembly 40 is inserted into the dermal layer of the skin, the housing 74 is in a lower position. The plunger 82 is then pulled upward with the housing 74 correspondingly moving upward against the outer wall 72 of the vacuum mechanism 70. As the housing 74 is raised upward, the volume of the inner chamber 76 increases which decreases the pressure adjacent to the proximal end 17 of the capillary tube 12. This results in a negative pressure which provides an additional force to urge interstitial fluid into the passageway 18 of the capillary tube 12.

The spacer member 60 is also designed to improve the flow of interstitial fluid into the capillary tube 12 in addition to controlling the depth of penetration of the needle assembly 40. As shown in FIGS. 2 and 6, the bottom edge 61 of the spacer member 60 compresses the skin 20 around the needle 42. This compression improves the flow of the interstitial fluid located in the dermal layer 24 into the capillary tube 12. Once a sample of interstitial fluid is drawn into and retained in the passageway 18 of the capillary tube 12, the constituents in the interstitial fluid may now be measured to determine the concentration of the constituent. Any pressure or vacuum is applied only to collect fluid. Such pressure or vacuum is not used to retain the fluid in tube 12 and is optional to enhance collection.

In accordance with the present invention, various methods of spectrophotometric analysis may be performed on constituents in the interstitial fluid once a sample has been retained in the capillary tube 12. These measurement techniques utilize a testing light of known intensity including a wavelength absorbable by the constituent being measured which is then directed toward the constituent of the interstitial fluid. Also, a reference wavelength is preferably utilized. A light detector is provided for measuring the intensity of the testing light being spectrally modified by the constituent. Based on absorption analysis, the concentration of the constituent can then be calculated. It will be appreciated that while several methods for calculating the concentration of the constituent are disclosed herein, various other methods may be utilized which incorporate light analysis to calculate the concentration of the constituent in the interstitial fluid.

Figure 5:
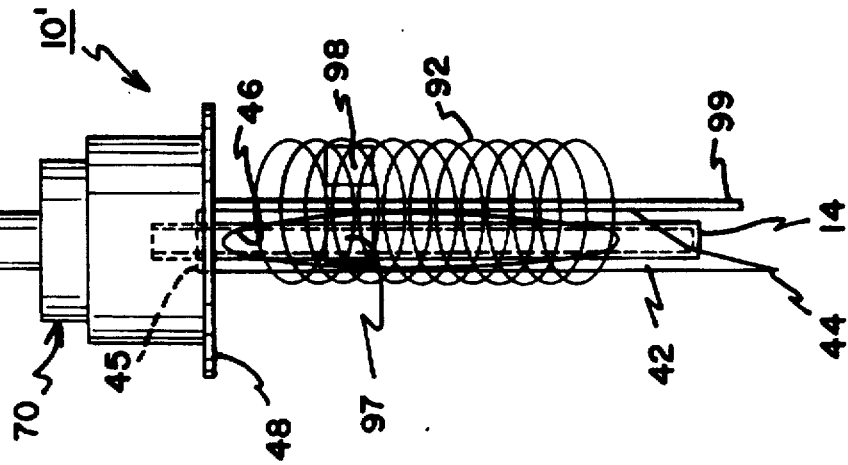
FIG. 5 is a front elevation view of the apparatus of FIG. 4.
Figure 5A:
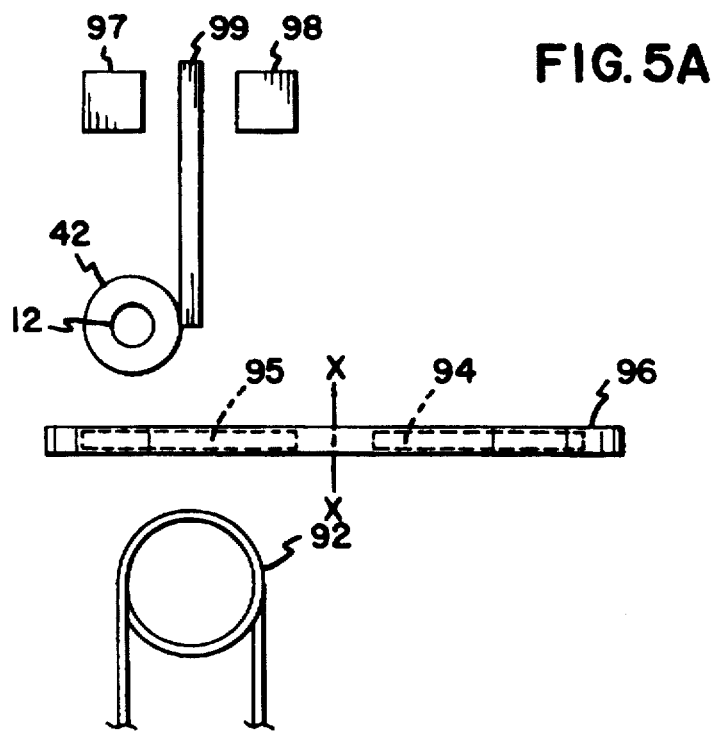
FIG. 5A is a top plan view of a detection apparatus.

FIGS. 4, 5 and 5A schematically illustrate the testing for blood glucose utilizing the present invention. After collection of interstitial fluid into the capillary tube through the above-mentioned apparatus and method, the spacer member 60 is removed. An infrared radiation source 92 (shown as a heating coil) is provided opposing the needle 42 and capillary tube 12. As indicated, the needle 42 has openings or slots 46 to permit infrared radiation to pass directly to and through the capillary tube 12.

Filters 94, 95 are contained on a wheel 96 placed between the infrared source 92 and the tube 12. The filters 94, 95 filter out energy at undesirable wavelengths such that only energy at wavelengths that contain useful information is allowed to enter the tube 12. For example, filter 94 passes a glucose absorbable test wavelength (e.g., 1040 wavenumber) and filter 95 passes a reference wavelength (e.g., 960 wavenumber). The filters 94, 95 are mounted in a chopping wheel 96 which revolves about axis X—X to allow energy to pass through different filters 94, 95 at different times. The filter 94 will preferably pass light at about 1040 wavenumbers for an absorption of glucose indication. Filter 95 will pass light at 960 wavenumbers to account for shifts in transmission at the glucose absorption number (1040 wavenumber) that are not attributable to glucose.

The infrared source 92 also generates heat which evaporates off the fluid contained within the capillary tube 12. As a result, the constituents of the interstitial fluid remain as a residue deposit on the interior wall of the capillary tube 12. The filtered infrared radiation (which is of a wavelength absorbable by blood glucose or any other constituent to be measured) passes through the IR transparent capillary tube 12. Positioned on a side of the capillary tube opposite the infrared radiation source are two detectors 97, 98. One detector 98 directly opposes the infrared radiation passing through the filter wheel 96. The other detector 97 opposes and is positioned to receive infrared radiation which is passed through the capillary tube 12. A knife edge 99 is provided between the two detectors to prevent the first detector 98 from receiving radiation which is passed through the tube 12 and to prevent the second detector 97 from receiving infrared radiation directly from the source 92. Preferably, the detectors 97, 98 are slidable on the knife edge 99 so that absorption along the length of the capillary tube can be measured. The detectors 97, 98 move along the direction of arrow A in FIG. 4. Alternatively, detectors 97, 98 may be fixed and the tube 12 and needle 42 may be axially moved. Finally, detectors 97,98 and tube 12 may remain relatively fixed as long as the residue deposit in tube 12 is uniform or the entire tube is within the detectors' field of view.

The detectors 97, 98 are preferably any type of detector that can detect infrared radiation and provide a signal indicative of the amount of infrared radiation detected. The detectors 97, 98 provide the signals to a circuit 100. The circuit 100 compares the received radiation as measured by the first detector 98 at a first period in time when reference filter 95 is in place and the radiation received at a second period of time when test filter 94 is in place and the measurements are ratioed. The signal received by the second detector 97 is similarly ratioed by the circuit. The two detectors' ratios are then ratioed by each other to produce a single number which is proportional to the concentration of glucose in the interstitial fluid sample. If required, the tube 12 can be measured prior to obtaining the sample in the same manner described above. This empty tube measurement can be used to account for material and geometry variations from tube to tube. It will be appreciated that the detectors and electronics for providing such an analysis form no part of this invention per se and may be such as that shown and described in U.S. Pat. No. 5,115,133.

By way of example, let:

$AB_{97}$=Energy detected by detector 97 with the absorption filter 94 between source 92 and tube 12;

$REF_{97}$=Energy detected by detector 97 with the reference filter 95 between source 92 and tube 12;

$AB_{98}$=Energy detected by detector 98 with the filter 94 between source 92 and detector 98; and $REF_{98}$=Energy detected by detector 98 with the filter 95 between source 92 and detector 98;

Ratio$_{TEST}$=(AB$_{97}$/REF$_{97}$) TEST/(AB$_{98}$/REF$_{98}$)$_{TEST}$

Where "TEST" indicates measurements taken through a tube 12 contain a fluid sample;

Ratio$_{START}$=(AB$_{97}$/REF$_{97}$) START/ (AB$_{98}$/REF$_{98}$)$_{START}$

Where "START" indicates measurements taken through an empty tube 12.

With the above definitions, Ratio$_{TEST}$ is inversely proportional to the glucose concentration in the measured sample. The relation between the ratio$_{TEST}$ and the concentration can be empirically measured and stored in the memory of circuit 100. With the circuit 100 receiving the readings of detectors 97,98, the ratio is easily calculated and compared to the memory to determine the concentration and provide a readout thereof. If material or geometry variations of the tube 12 cannot be controlled, the ratio of Ratio$_{TEST}$/Ratio$_{START}$ can, alternatively, be used to compare to the empirical data to determine blood glucose concentration.

From the foregoing, the reader will note that a preferred embodiment to the present invention includes drying of the collected sample by means of heating the capillary tube 12 with the infrared source 92 in order to evaporate the liquid from the capillary tube 12. The drying measurement provides numerous advantages. Optical measurement allows quantitative analysis of fluid volumes too small to be otherwise chemically analyzed. Also, evaporating the liquid from the tube 12 removes water which is the major energy absorber in a wet measurement system. As a result, the accuracy of the measurement is increased because there is no need to distinguish energy absorption of an analyte (for example, glucose) from IR absorption by water. Also, when performing infrared spectrometry of analytes in solution, the path length must be measured accurately or an apparent path length accurately determined.

In the event a dry method is used, it is preferable to first measure the height which the fluid achieves in the capillary tube 12. Since the capillary tube 12 diameter is predetermined (within manufacturing tolerances), the volume of the withdrawn fluid can be measured before driving off the fluid with heat from source 92. When the amount of glucose within tube 12 is determined through the dry technique by passing the sensors 97, 98 along the length of the tube 12, the concentration can be calculated since the volume of the fluid has been pre-measured.

In the event a wet measurement technique is desired (i.e., measuring the glucose level of the fluid without first evaporating the fluid from the tube 12), the apparatus of FIGS. 7–10 is preferably employed.

Figure 8:
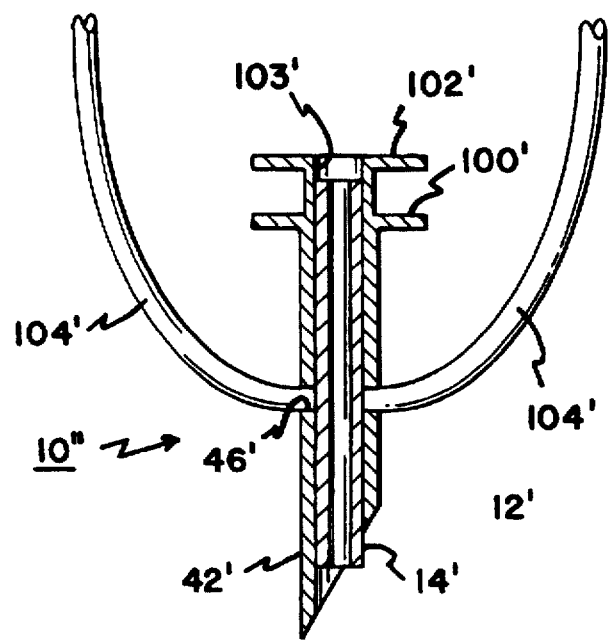
FIG. 8 is a front sectional view of the apparatus shown in FIG. 7 with light transmitting and detecting devices secured to the apparatus.
Figure 9:
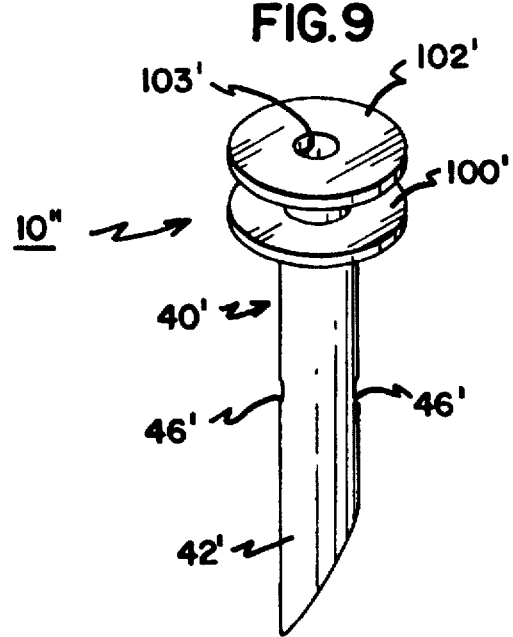
FIG. 9 is a prospective view of the apparatus shown in FIG. 7.
Figure 11:
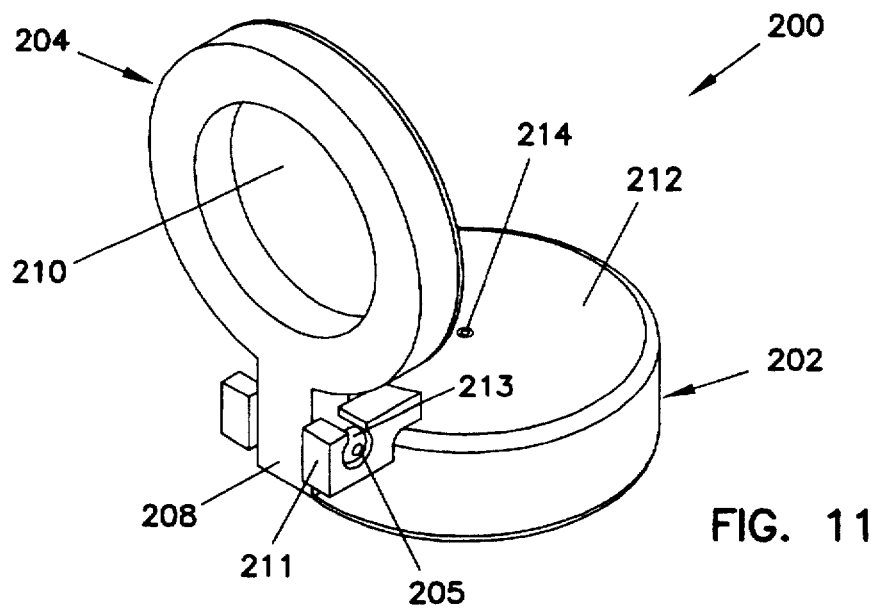
FIG. 11 is a perspective view of a sampler according to an alternative embodiment of the present invention with a cover shown in the open position.
Figure 12:
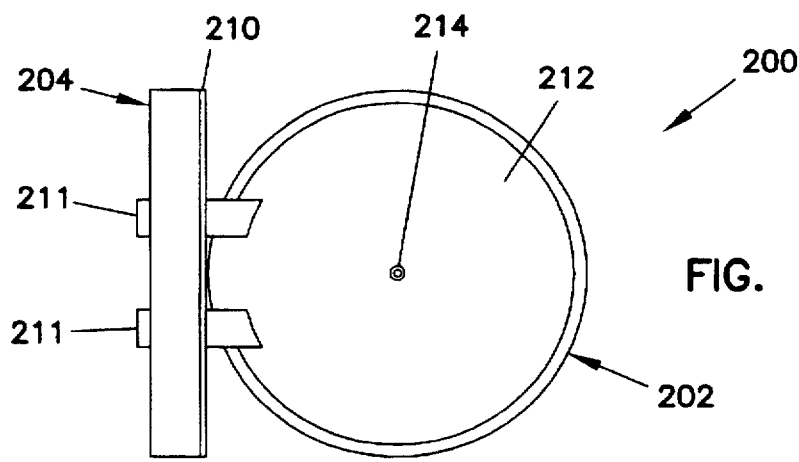
FIG. 12 is a top plan view of the sampler of FIG. 11.
Figure 13:
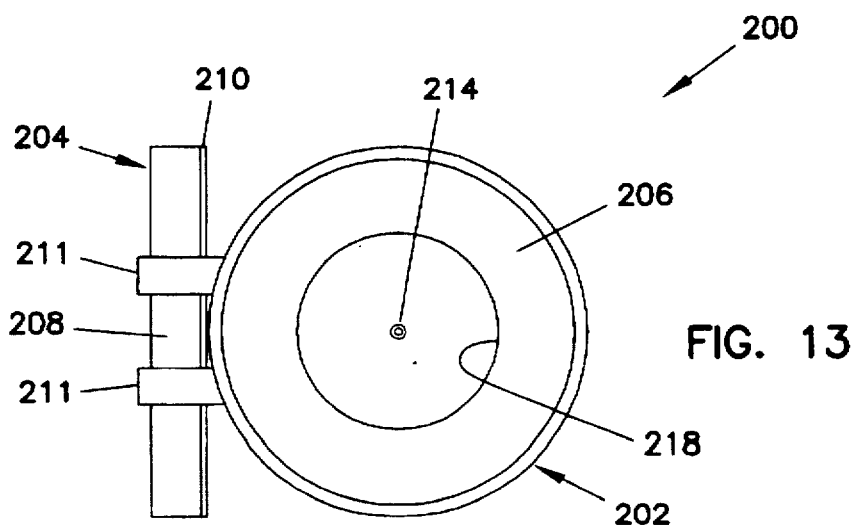
FIG. 13 is a bottom plan view of the sampler of FIG. 11.
Figure 14:
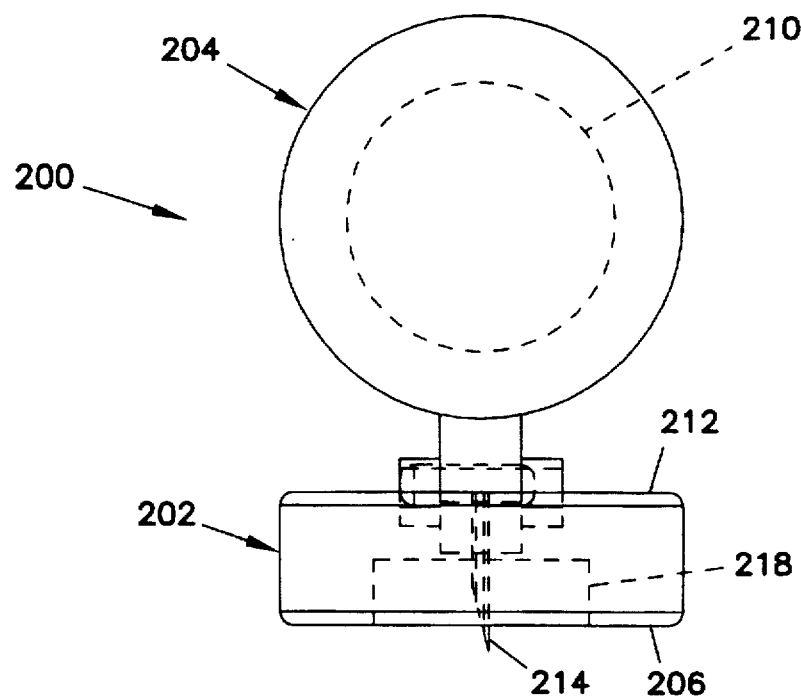
FIG. 14 is a rear elevation view of the sampler of FIG. 11.
Figure 15:
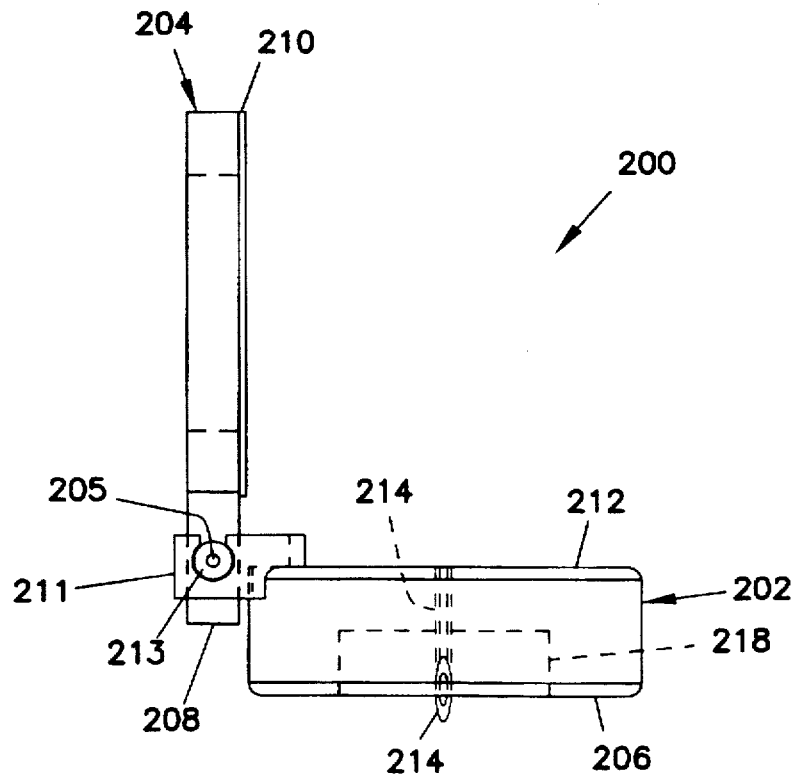
FIG. 15 is a side elevation of the sampler of FIG. 11.
Figure 18:
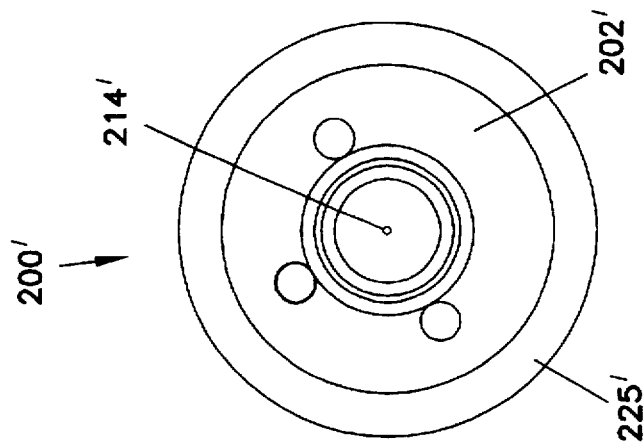
FIG. 18 is a bottom plan view of the sampler of FIG. 16.
Figure 17:
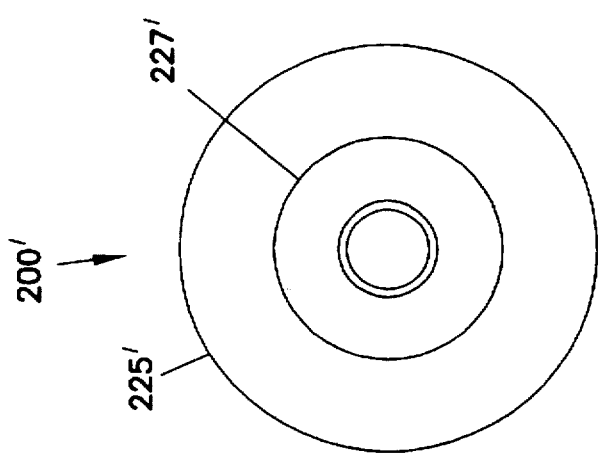
FIG. 17 is a top plan view of the sampler of FIG. 16.
Figure 16:
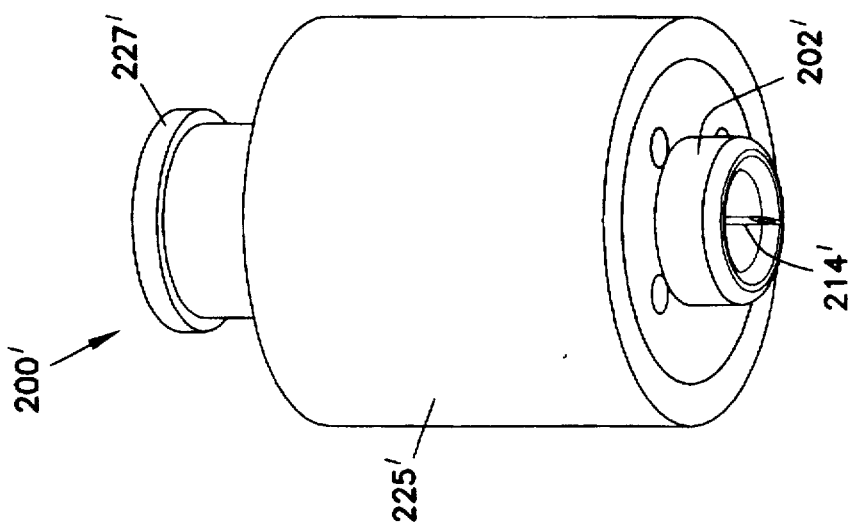
FIG. 16 is a perspective view of a still further alternative embodiment of a sampler according to the present invention.
Figure 20:
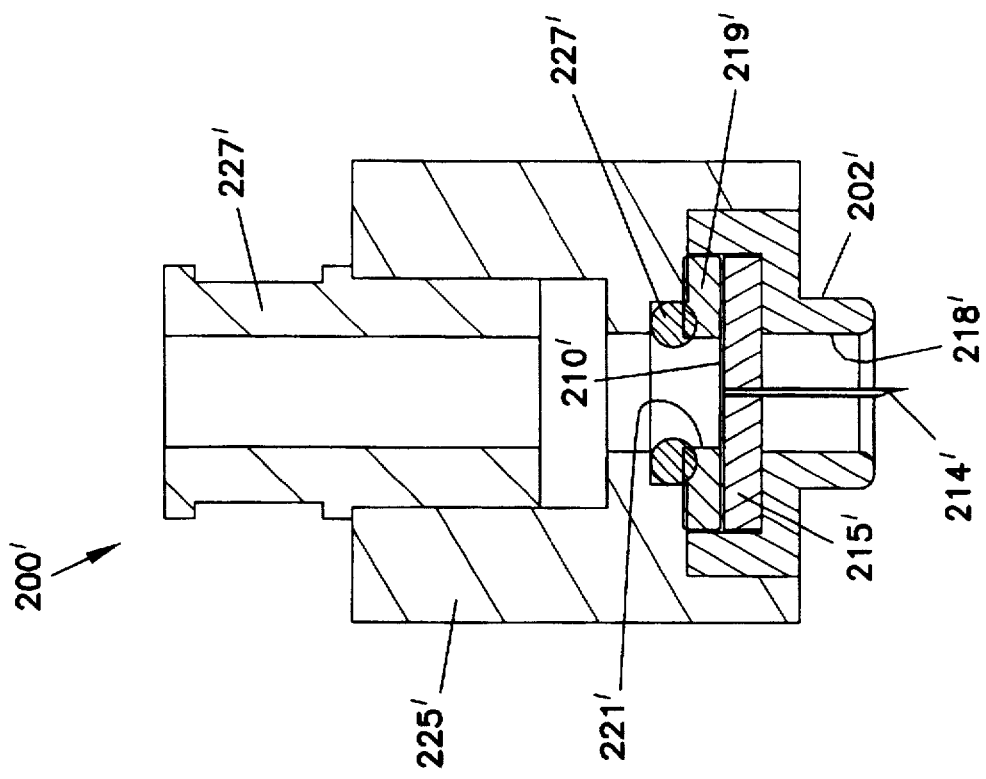
FIG. 20 is a view taken along lines 20—20 of FIG. 19.
Figure 19:
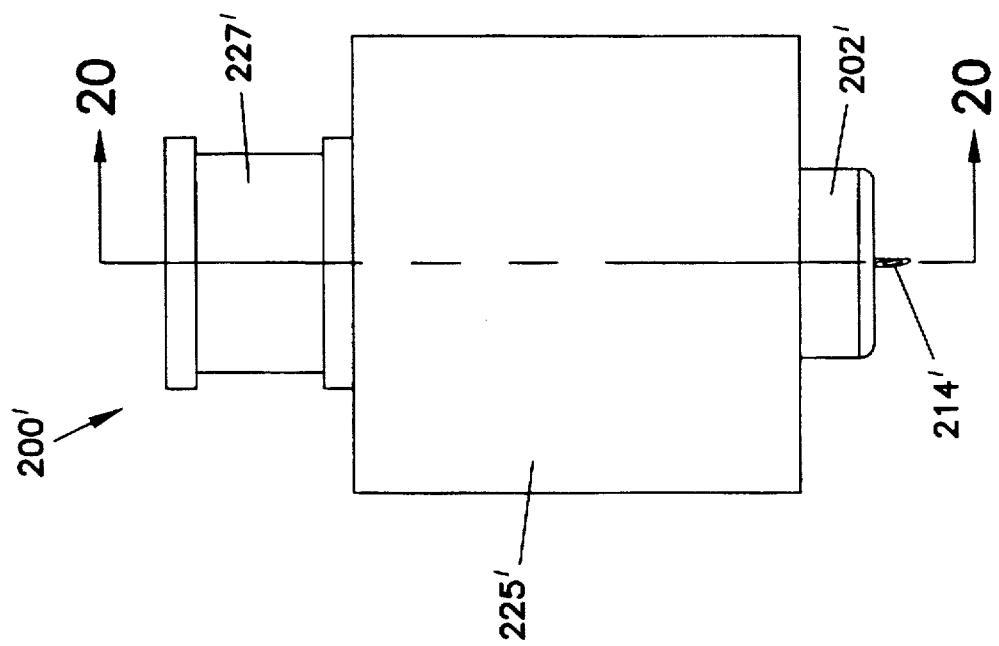
FIG. 19 is a side elevation view of the sampler of FIG. 16.

As discussed previously, a variety of structures may be utilized as the collection apparatus according to the principles of the present invention. Referring now to FIGS. 7–9, an alternative embodiment of the present invention is shown. This alternative collection apparatus 10" similarly includes a hollow needle 42' and a hollow capillary tube 12' open at both ends and securely disposed within the needle 42'. The needle 42' includes a first flange 100' disposed against the outer wall of the needle 42' to control the depth of the penetration of the needle. As shown in FIG. 7, the collection apparatus 10" is inserted into the skin 20' until the flange 100' rests against the surface of the skin 20'. In this position, the distal end 14' of the capillary tube 12' is disposed within the upper third portion of the dermal layer 24 of the skin and the capillary action of the tube 12 draws interstitial fluid into the passageway 18' of the tube 12' to collect the sample. It is appreciated that a vacuum mechanism could also be adapted for use with this collection apparatus to assist the flow of interstitial fluid into the capillary tube.

The proximal end of the needle 42' includes a gripping flange 102' which provides a handle for inserting and removing the collection apparatus 10" from the skin 20. Flange 102' is open at 103' to vent capillary tube 12'. The needle 42' includes diametrically opposing apertures 46' for exposing a portion of the capillary tube 12'. After a sample of interstitial fluid has been collected within the capillary tube 12', the collection apparatus 10" is removed from the skin 20 and a testing light source (preferably transmitted through optical fibers 104' shown in FIG. 8) is then directed through the apertures 46' to determine the concentration of a constituent in the interstitial fluid.

In a wet technique, the liquid within the tube 12' is not evaporated. Instead, infrared radiation having a wavelength absorbable by glucose is passed through the apertures as illustrated in FIG. 8. If the diameter of the tube 12 is strictly controlled and known, the actual path length of the infrared radiation is known. However, if the diameter cannot be strictly controlled, the path length can be measured through interferometry techniques. With knowledge of the actual path length, it is well within the skill of the art to determine the amount of glucose based on the absorbed infrared radiation and to account for absorption attributable to liquid within the path length.

Figure 10:
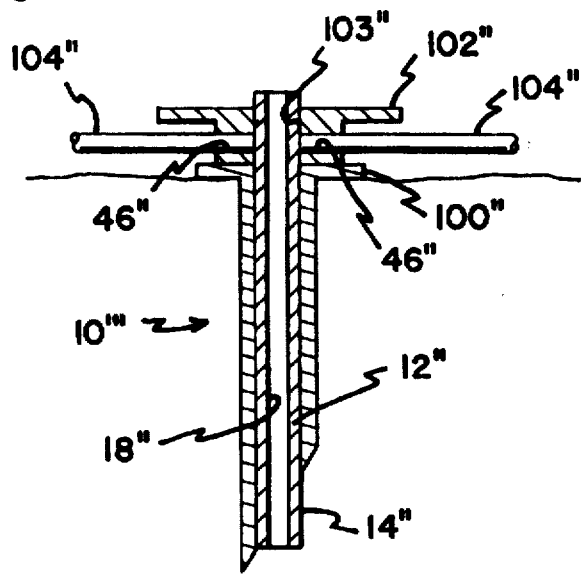
FIG. 10 is a further alternative embodiment of the apparatus of FIG. 7.

FIG. 10 shows a still further embodiment of the invention in an apparatus 10'". In this embodiment (in which elements in common to FIG. 8 are numbered identically with the addition of two apostrophes), apertures 46" are positioned between flanges 100", 102". With this construction, optical fibers 104" may be installed and spectrometrically testing fluid within tube 12" while the apparatus 10'" is in situ with flange 100" pressed against a skin layer.

The foregoing description identifies structure and apparatus and methods of testing which eliminate certain of the disadvantages of the prior art. With respect to prior invasive techniques, the present invention provides for collecting a sample of interstitial fluid in the dermal layer 24 of the skin utilizing a needle 42 and capillary tube 12 having a small diameter to minimize the pain of the needle penetration. Additionally, prior invasive techniques require the presence of a large concentration of blood vessels and coincidentally associated nerve endings (i.e., such as a fingertip) which increases the pain of the needle or lanset penetration. The present invention does not have these requirements since it is collecting interstitial fluid from the dermal layer 24 of the skin 20 and thus may be used on any area of the skin with minimal pain to the user. With regard to prior non-invasive techniques, the minimally invasive optical testing of the present invention provides for a more accurate reading of the glucose concentration of bodily fluids. A significant advantage is measurement of glucose in interstitial fluid rather than through tissue and whole blood. The interstitial fluid has the same glucose information, but is in a more easily tested form resulting in a more reliable measurement. Blood contains more interferents to IR glucose testing and possibly in higher concentrations than interstitial fluid (such interferents include blood cells, cholesterol and protein).

D. Interstitial Fluid Sampling And Alternate Testing Techniques

The foregoing discussion of the present invention illustrates a collection of interstitial fluid and passing infrared light through a volume of the collected fluid (either before or after drying) in order to determine blood glucose levels. However, the collection method and apparatus of the present invention can be utilized in a variety of different embodiments for measurement of blood glucose or other fluid constituents.

With reference to FIGS. 11–14, an alternative embodiment is shown for an interstitial fluid sampler 200. The sampler 200 includes a base 202 and a cover 204 connected together at a hinge point 205. Shown best in FIG. 11, the cover 204 is a ring having an extension 208. The extension 208 cooperates with supports 210 and a pivot pin 212 to define the hinge point 205.

An interior surface of the cover 204 is provided with a membrane 210 covering the interior surface of the cover 204. The base 202 has a flat upper surface 212. In FIGS. 11–14, the cover 204 is shown pivoted to an open position. The cover 204 may be pivoted about hinge point 205 to a closed position with the membrane 210 resting against and opposing the upper surface 212 of base 202.

Secured to the base 202 and extending axially therefrom is a needle 214. The needle 214 protrudes beyond the lower surface 206 of the base 202. The needle terminates at the upper surface 212 and flush therewith. Formed in the base 202 and exposed through the lower surface 206 is a chamber 218. The chamber surrounds the needle 214.

With the construction thus described, the cover 204 may be placed in a closed position with the membrane 210 abutting surface 212. Accordingly, the membrane 210 is also opposing the needle 214. The base lower surface 206 is urged against a patient's skin such that the needle 214 penetrates into the skin. Interstitial fluid is drawn or forced through the needle 214 resulting in a spot of the interstitial fluid being placed on the membrane 210. In this manner, a sample of interstitial fluid is collected on the membrane 210.

With the membrane 210 containing a sample of interstitial fluid, the interstitial fluid may now be tested for constituents. The testing of the sample of interstitial fluid collected on membrane 210 can be done in any number of ways. For example, the cover 204 may be pivoted to the open position shown in FIGS. 11–14. The collected interstitial fluid will appear as a spot on the membrane 210. Infrared light may be passed through the spot of interstitial fluid on the membrane 210 with absorption of the IR wavelengths indicating the amount by which desired constituents (for example, glucose) are present. Alternatively, the sample can be electro-chemically tested. Electro-chemical testing of blood glucose is done with miniature sensors such as those discussed in an article entitled "Towards Continuous Glucose Monitoring: In Vivo Evaluation Of A Miniaturized Glucose Sensor Implanted For Several Days In Rat Subcutaneous Tissue", Moatti-Sirat et al., *Diabetologia* (1992) pages 224–230. Other electrodes for testing blood glucose are discussed in an article entitled "An Overview of Minimally Invasive Technologies", Ginsberg et al., *Clinical Chemistry*, Volume 38, No. 9, 1992. As an additional alternative, collected samples can be colormetrically tested. In colormetric testing, the membrane 210 may be a multilayer of paper and chemicals. As the interstitial fluid passes through the layer, the color changes. The changing color indicates relative amounts of glucose concentration. An example of such is discussed on page 26 in May 1993 issue of *Diabetes Forecast*. Another alternative is an ATR (attenuated total reflectance) measurement of the collected fluid. In the ATR method, the collected fluid is passed over an ATR crystal, which may be part of the fluid collection device. An IR beam is directed into the ATR crystal, and the evanescent wave of the beam is preferentially absorbed at specific wave lengths indicating the amount by which desired constituents (such as glucose) are present. Other potential techniques for analyte measurement include luminescence, immunilogical, radioistopic, and others.

In the embodiment of FIGS. 11–15, the interstitial fluid is collected on the membrane 210. In a preferred embodiment, the membrane 210 is a microporous material (e.g., nylon) which will provide even wetting and drying. The membrane should have a high surface area to promote rapid drying. An example of such a membrane is a 0.2 micron pore size of Nylaflo. Nylaflo is a registered trademark for a nylon disk made by Gelman Science, Inc. of Ann Arbor, Mich. Preferably such materials are IR transparent at the absorption wavelength of the constituent being measured. Other examples of membranes are polyethylene, polyacylonitrile (PAN), poly(styreneacrylonitrile) (SAN) and polyamides (nylon). While the foregoing are high IR transmissive, less IR transmissive materials may be suitable. These include polysulfone, polyethersulfone (PES), cellulosics, poly (vinylidene fluoride) (PVDF), poly(ethylene terephthalate) (PET) and polycarbonate. The membrane material can be formed in a variety of suitable ways including woven, nonwoven, felted and as a paper.

The needle 214 is preferably as small as possible to avoid pain to a user. For example, needle 214 will be of a size of about 28 to 32 gauge (i.e., 0.36 millimeters outside diameter to 0.23 millimeters outside diameter) with a presently anticipated preferred size of about 29 gauge. The preferred gauge is limited by the mechanical integrity of commercially available needles. Also, while needle 214 could be sized and have a length sufficient to extend into the subcutaneous tissue and still be within the intended scope of the present invention, needle 214 will preferably be sized to penetrate into the dermis. As previously discussed, the minimum size of the needle 214 and selection of its length to penetrate into the dermis are made to minimize the possibility of contact with nerves or penetration of blood vessels.

The apparatus and method of the present invention is intended to remove interstitial fluid rather than penetrate a blood vessel and remove blood. While it is anticipated some blood may be in the interstitial fluid, it is the desire of the present invention to minimize or avoid the presence of blood being collected by the sampler. The present invention utilizes the membrane 210 which ensures a uniform thickness and absorption such that the amount of fluid collection per volume of the membrane is constant within the region of the spot on the membrane 210 at which the interstitial fluid is deposited. Also, with the present invention, the membrane 210, can be easily dried. For example, in most instances, due to the small amount of fluid being deposited on the membrane 210, the membrane will dry in ambient conditions. If desired, the membrane 210 may be subjected to any heating or blowing in order to thoroughly dry the membrane 210. Removal of water from the collected sample enhances the measurement for glucose. For example, in a paper entitled "Quantitative Analysis of Aqueous Solutions by FTIR Spectroscopy of Dry-Extract" by DuPuy et al., *SPIE*, Volume 1575, 8th International Conference on Fourier Transform Spectroscopy (1991), pages 501–502, the greater identifiability of the IR signature of a dry sucrose extract is shown with reference to an absorption spectrum of sucrose and water.

The spacing of the needle 214 from the walls of the base 202 by means of the cavity 218 is for the purpose of providing the surface 206 to form an annular ring surrounding the needle 214 which forces down on a patient's skin to urge interstitial fluid into the needle 214 as previously illustrated and discussed with reference to FIGS. 2 and 6.

FIGS. 16–20 show a still further embodiment of the present invention and illustrate a sampler 200'. Sampler 200' includes a base 202' having a chamber 218' through which a needle 214' passes. The needle 214' is secured to a plate 215'. The plate 215' rests within an upper chamber 218a' of base 202'. The plate 215' is secured from rotational movement relative to the base 202' by means of an alignment pin 217' passing through both the base 202' and the needle plate 215'.

A membrane 210' such as the aforementioned Nylaflo (membrane 210) is secured by adhesive or mechanical connection or the like to a membrane ring 219'. The membrane ring 219' and membrane 210' are placed against the needle plate with the membrane 210' opposing the needle 214'.

The membrane ring 219' has an axial hole 221' through which an interstitial fluid spot may be viewed after depositing of the spot on the membrane 210' by reason of the interstitial fluid passing through the needle 214'. The membrane ring 219' has a hole 223' to receive the alignment pin 217'. A main housing 225' is placed over the body 202' with an O-ring 227' positioned to space the spacer 202' from the housing 225'. An additional hub 227' is placed within the housing 225' such that a vacuum source or the like may be applied to the hub 227' if desired to assist in the draw of interstitial fluid up the needle 214'. It will be appreciated that the needle 214' and membrane 210' as well as the spacing on the needle 214' from the walls 218' are done for the purposes previously described.

With the construction thus described, the bottom surface 206' of the base 202' is placed against the patient's skin, interstitial fluid is drawn up through the needle 214' and deposited as a spot on the membrane 210'.

The membrane ring 219' with the attached membrane 210' may be removed and the spot tested for constituency concentrations as previously described.

Figure 21:
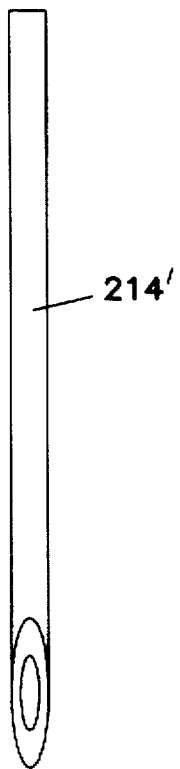
FIG. 21 is side elevation view of a needle for use in the sampler of FIG. 16.
Figure 22:
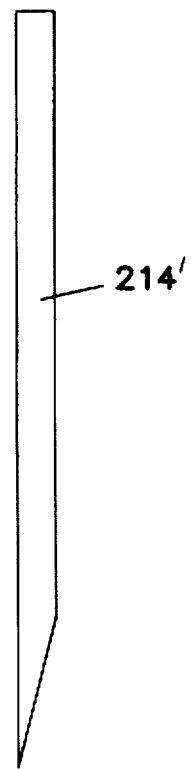
FIG. 22 is the view of FIG. 21 rotated 90°.
Figure 23:
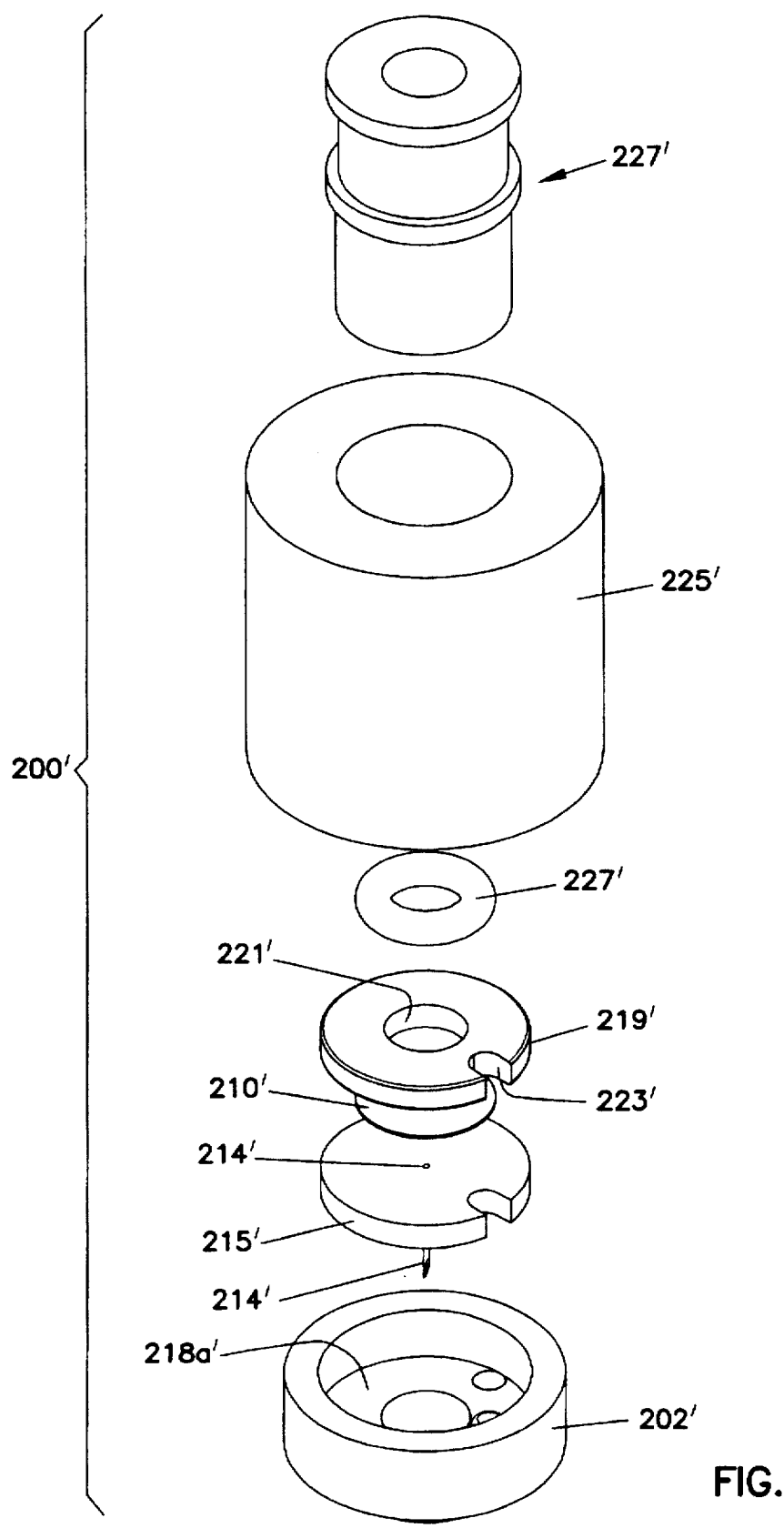
FIG. 23 is an exploded perspective view of the sampler of FIG. 16.

FIGS. 21–22 show a still further alternative embodiment of the present invention by means of a sampler 200". The sampler 200" includes a base portion 202" having a bottom surface 206" with an axially positioned chamber 218". The base 202" also has a flat upper surface 212". A needle with the dimensions and structure previously described extends axially through the base 202" with the needle protruding below the lower surface 206" and flush with the upper surface 212". A membrane 210" of Nylaflo is positioned on the upper surface 212" in overlying relation to the needle 214". The sampler 200" also includes a centrally positioned handle 215" to permit a user to grasp the sampler between opposing thumb and forefinger to force the surface 206" against the patient's skin resulting in penetration of the needle 214". Interstitial fluid is passed through the needle 214" and deposited on the membrane 210". Unlike the membrane 210 of FIGS. 11–14 or the membrane 210' of FIGS. 16–20, the sample on the membrane 210" may be tested by reflecting infrared light through the sample and off of surface 212". In the previous examples, infrared light is passed through the membrane rather than reflected.

Other examples of sampling apparatus according to the present invention include a sheet of metal (e.g., a small lance having the sizing recited above with respect to the needles 214,214',214" to avoid pain and blood collection). A membrane such as the material of membranes 210,210',210" is deposited on the sheet of metal such that interstitial fluid is drawn onto the membrane through capillary wicking or similar action upon insertion of the sheet metal into the patient's skin. A still further example includes a penetration member in the form of a split sheet of metal having a slit defined between opposing surfaces of the metal. The split sheet has the foregoing recited dimension for pain and blood avoidance. Upon insertion of the sheet into the skin, interstitial fluid is drawn into the slit. The fluid may be deposited on a membrane for IR testing.

Figure 26:
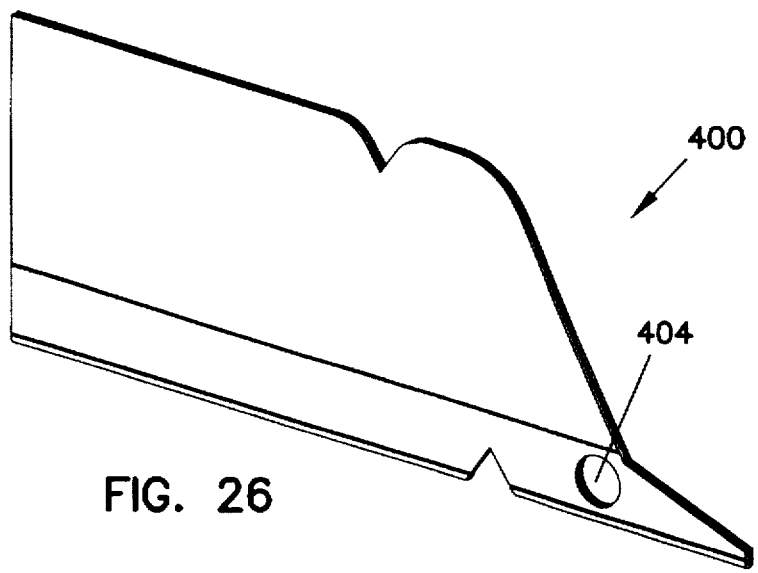
FIGS. 26–31 illustrate a split sleeve penetration member.
Figure 27:
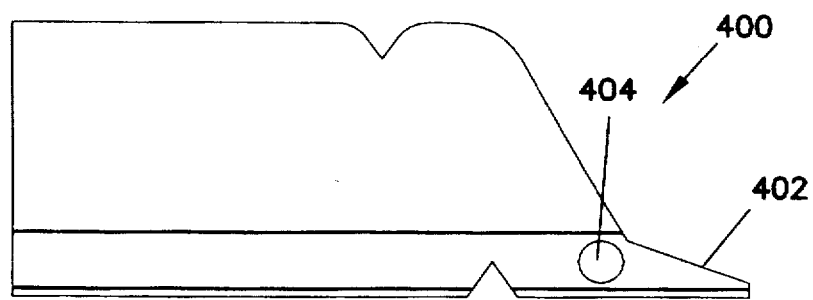
Figure 28:
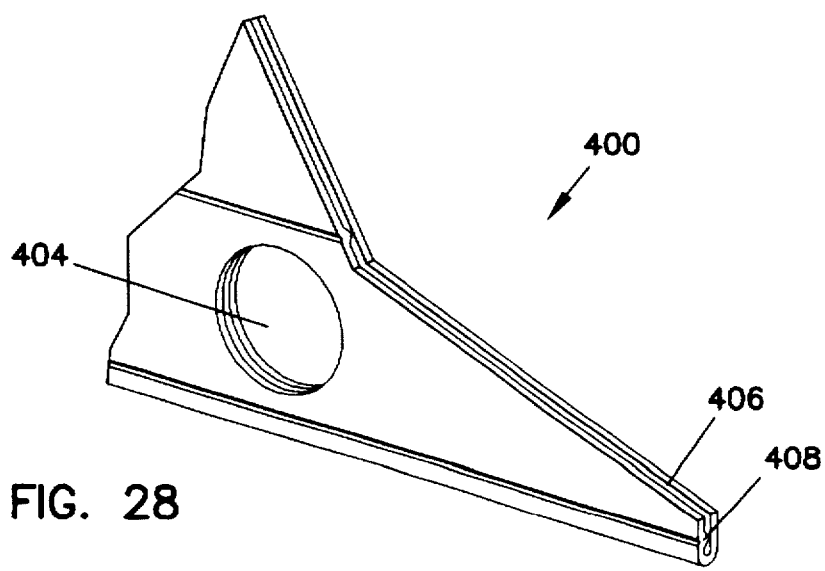

The split sleeve penetration member is illustrated in two embodiments in FIGS. 26–31. In FIGS. 26–28, a split sleeve 400 is shown in the form of folded metallic member having an angled leading edge 402. Cutouts are provided in the split sleeve 400 to define a cutout area 404 into which a membrane such as membrane 210 can be placed to receive collected fluid. The folded over metal of the split sleeve 400 defines a slot 406 which is maintained in spaced relation by reason of protruding rib 408 to prevent complete closure of the slot 406. The leading end 402 is sized similar to the needles 214 such that the leading end 402 may be inserted into the skin with minimal pain and blood loss and with the advantages previously described. Interstitial fluid is drawn or urged through the slot 406 and deposited on the membrane (not shown but contained within area 404) for testing as previously described.

Figure 24:
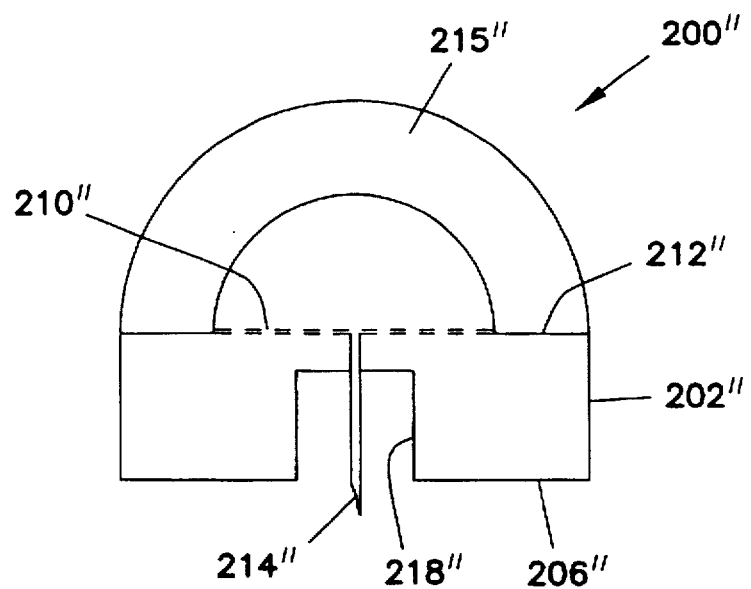
FIG. 24 is a side elevation view of a yet further embodiment of the present invention.
Figure 25:
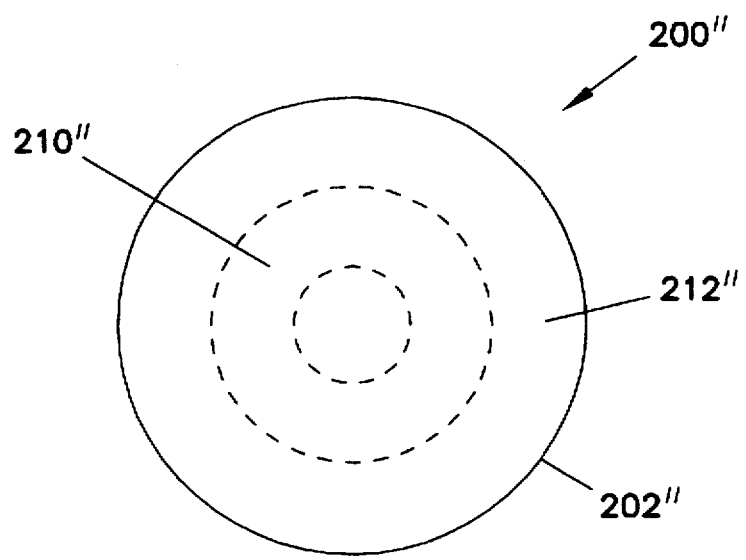
FIG. 25 is a top plan view of the sampler of FIG. 24.
Figure 29:
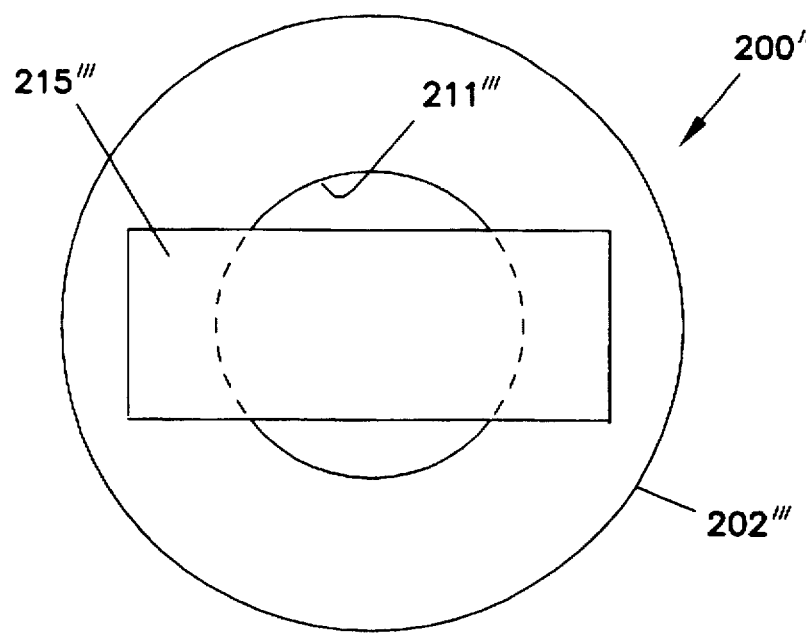
Figure 30:
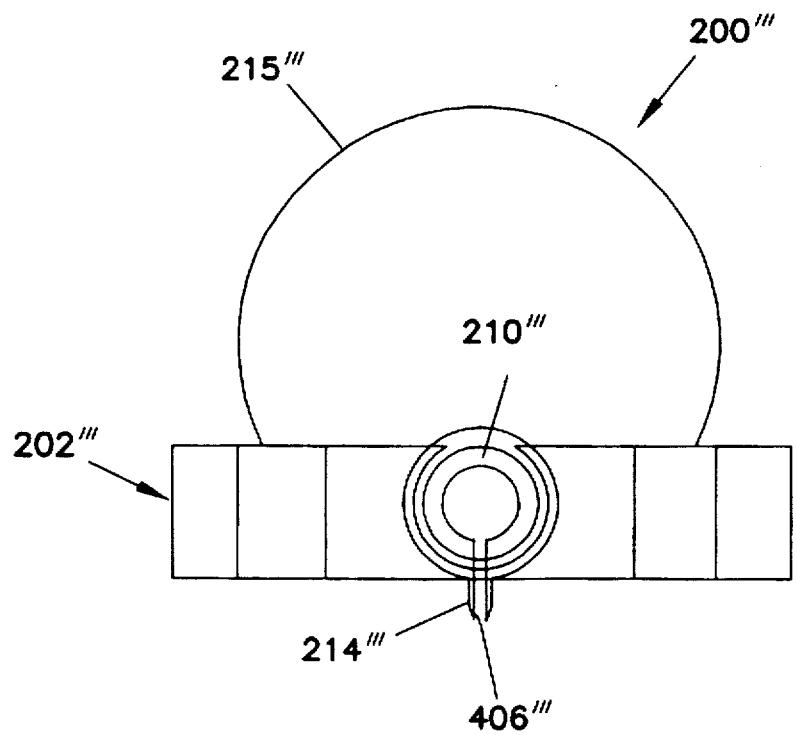
Figure 31:
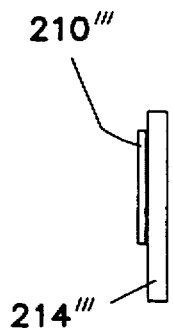

FIGS. 29–31 show an embodiment similar to that of FIGS. 24–25 of a sampler 200''' having a base member 202''' in the form of a ring and a handle 215'''. The ring includes a cutout central area 210'''. Connected to the handle 215''' and extending through the cutout area 210'" is a split sleeve penetration member 214'" which includes a metallic needle end having spaced-apart metallic portions to define a slot 406'" into which fluid can be passed and deposited on a membrane 210'". The size of the penetration member 214'" is similar to the sizing of needle 214" for the advantages previously discussed.

Through the foregoing detailed description of the present invention, it has been shown how the objects of the present invention have been obtained in a preferred manner. However, modifications in equivalence of the disclosed concepts, such as those which would readily occur to one skilled in the art, are intended to be included within the scope of the claims of the present invention.

What is claimed is:

1. A method for testing a sample of body fluid, said method comprising:

urging a sampler against a patient's skin, said sampler including a penetration member sized to penetrate the patient's skin into but not substantially through a dermal layer upon placement of said sampler against said skin;

drawing a sample of said fluid along said penetration member and out of said skin;

testing said sample for desired constituents.

2. A method according to claim 1 wherein said sample is tested by passing light through said sample and measuring an absorption of predetermined wavelengths.

3. A method according to claim 1 wherein said sample is tested electro-chemically.

4. A method according to claim 1 wherein said sample is tested colormetrically.

5. A method according to claim 1 wherein said sample is tested by attenuated total reflectance.

6. A method according to claim 1 wherein said penetration member is a needle selected to have a size smaller than 28 gauge.

7. A method according to claim 1 comprising compressing against said skin in a region surrounding said penetration member during placement of said sampler against said skin.

8. A method according to claim 1 comprising drying said fluid prior to said testing.

9. A method according to claim 1 comprising retaining said fluid on a membrane for said testing.

10. A method for determining a level of a constituent in a body fluid, said method comprising:

inserting a conduit into the dermal layer of skin but not through the dermal layer;

passing a sample of said body fluid located within the dermal layer into said conduit;

evaporating the liquid from said conduit so that only the constituent remains on the walls of the conduit; and directing a light source through the constituent retained in said conduit to determine the level of a constituent in the body fluid.

11. A method according to claim 10 wherein said light source includes light having a wavelength absorbable by the constituent and said step of directing the light source through the constituent includes measuring the amount of light absorbed by the constituent to determine the concentration of the constituent in the body fluid.

* * * * *